United States Patent [19]

Olson

[11] 4,225,514

[45] Sep. 30, 1980

[54] PROCESS FOR PREPARATION OF POLYENE ALDEHYDES

[75] Inventor: Gary L. Olson, Westfield, N.J.

[73] Assignee: Hoffmann-La Roche Inc., Nutley, N.J.

[21] Appl. No.: 917,607

[22] Filed: Jun. 21, 1978

Related U.S. Application Data

[60] Division of Ser. No. 849,148, Nov. 7, 1977, abandoned, which is a division of Ser. No. 731,056, Oct. 8, 1976, Pat. No. 4,071,538, which is a division of Ser. No. 618,708, Oct. 1, 1975, Pat. No. 3,997,529, which is a continuation-in-part of Ser. No. 594,377, Jul. 9, 1975, abandoned.

[51] Int. Cl.$^3$ ............................................. C07C 45/60
[52] U.S. Cl. ................................................... 568/447
[58] Field of Search ........................................ 260/598

[56] References Cited

U.S. PATENT DOCUMENTS

| | | | |
|---|---|---|---|
| 2,730,549 | 1/1956 | Isler et al. | 260/598 |
| 3,922,308 | 11/1975 | Derfer et al. | 260/598 |

FOREIGN PATENT DOCUMENTS 1167325  4/1964  Fed. Rep. of Germany ........... 260/598

OTHER PUBLICATIONS

Makin, Russian Chemical Reviews 38(3), [1969], 237–248.

*Primary Examiner*—Bernard Helfin
*Attorney, Agent, or Firm*—Jon S. Saxe; Bernard S. Leon; George W. Johnston

[57] ABSTRACT

A novel process for the preparation of polyene aldehydes which employs as starting materials, substituted 2H pyrans. Novel substituted 2H pyrans and polyene intermediates are also disclosed.

5 Claims, No Drawings

PROCESS FOR PREPARATION OF POLYENE ALDEHYDES

This application is a division of application Ser. No. 849,148, filed Nov. 7, 1977, now abandoned, which in turn is a division of U.S. Patent Application Ser. No. 731,056, filed Oct. 8, 1976, now U.S. Pat. No. 4,071,538, which in turn is a division of U.S. Patent Application Ser. No. 618,708, filed Oct. 1, 1975, now U.S. Pat. No. 3,997,529, which in turn is a continuation-in-part of U.S. Patent Application Ser. No. 594,377, filed July 9, 1975, now abandoned.

BACKGROUND OF THE INVENTION

The invention is directed to the preparation of polyene belonging to the vitamin A and carotenoid series. In view of the extensive role that these materials play in the physical well-being of humans and animals and in the coloring of foods, there is a constant on-going effort to find methods of producing polyenes in an economical and efficient manner.

The invention disclosed and claimed herein employs 2-substituted-6-alkoxy-3,6-dihydro-2H-pyrans as starting materials to prepare polyene aldehydes. The 2H pyrans utilized herein are prepared by Wittig reactions on the products derived from the Diels-Alder reaction of 1-alkoxydienes and glyoxal or glyoxylic esters.

The preparation of simple 2-alkoxy-5,6-dihydro-2H-pyrans has been previously reported in the literature. Kubler, *J. Org. Chem.*, 27, 1435 (1962), describes the preparation of such 2H dihydropyrans by the reaction of paraformaldehyde and 1-alkoxydienes. Shavrygina et al., *J. Org. Chem., USSR*, 2, 1394 (1966), disclose the preparation of certain 2-substituted-6-alkoxy-3,6-dihydro-2H-pyrans via the condensation of 1-alkoxydienes with paraform, chloral, and ethyl glyoxylate. The obtention of 6-alkoxy-3,6-dihydro-2H-pyran-2-carboxylic acid derivatives by the condensation of 1-alkoxydienes with esters of glyoxylic acid is disclosed by Konowal et al., *Rocz. Chem.*, 42, 2045 (1968) and by Makin, *Russ. Chem. Rev.*, 38, 237 (1969). There has been an extensive series of articles related to the use of 2-substituted-3,6-dihydro-2H-pyrans as starting materials for the synthesis of monosaccharides. Among such articles are Chimelewski et al., *Rocz. Chem.*, 46, 627 (1972); Zwierzchowska et al., *Rocz. Chem.* 44, 1587 (1970).

In addition to the above-mentioned studies with 1-alkoxydienes, Zwierzchowska-Nowakowska et al., *Rocz. Chem.* 48, 1928 (1974), describes the Diels-Alder condensation of 1-acetoxy-1,3-butadiene with butyl glyoxylate to form acetoxy-substituted 2H dihydropyrans.

The article by Makin, (supra), discusses the syntheses of 1-alkoxydienes and their oligomerization to form polyenes. Particularly illustrated is the condensation of α,β-unsaturated aldehydes with 1-alkoxydienes and subsequent conversion of the reaction products to polyenals. Compounds such as 5-ethoxycitral, 5,9-diethyloxyfarnesal and others were obtained according to this method.

A mechanism for the condensation reaction between α,β-unsaturated aldehydes and 1-alkoxydienes, proceeding via the intermediacy of a dihydropyran is proposed in Makin (by reference to an article by Krasnaya et al.), but the Krasnaya et al. article appearing in *Zhurnal Obshchei Khimii*, 30 (12), pp 3918–3926, 1960, indicates that the mechanism is not as proposed, and that dihydropyrans are not intermediates.

The preparation of polyene aldehydes of the vitamin A and carotene series via the reaction products of 1-alkoxydienes with glyoxal and glyoxylic esters, has been unknown heretofore.

The instant invention provides the art with a novel, efficient and economical method of preparing the above-mentioned polyene aldehydes.

SUMMARY OF THE INVENTION

This invention is directed to the preparation of a polyene aldehyde having the formula:

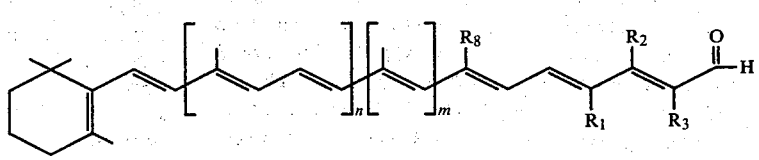

wherein $R_1$, $R_2$, $R_3$ and $R_8$ are hydrogen or methyl and m and n are integers equal to 0 or 1; comprising the steps of reacting a compound having the formula:

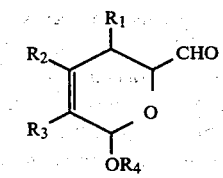

wherein $R_1$, $R_2$ and $R_3$ are as above; and $R_4$ is lower alkyl; with a phosphonium salt of the formula:

wherein $R_5$, $R_6$ and $R_7$, which may be the same or different, are selected from the group consisting of lower alkyl, aryl, and aryl lower alkyl; $R_8$ is as above and $R_9$ is

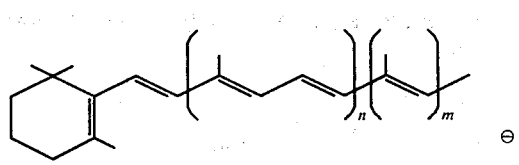

where m and n are as defined above, and X is an anion; in the presence of base to form a compound of the formula:

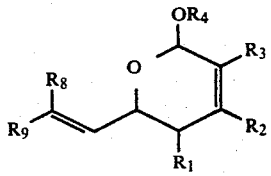

wherein $R_1$, $R_2$, $R_3$, $R_4$, $R_8$ and $R_9$ are as previously defined; followed by treatment with a catalyst to form compound I.

DETAILED DESCRIPTION OF THE INVENTION

The term "lower alkyl", as used herein, denotes straight or branched chain saturated hydrocarbon groups of 1 to 6 carbon atoms, for example, methyl, ethyl, propyl, butyl and the like. As further used herein, the term "lower alkoxy" denotes alkoxy groups having 1 to 6 carbon atoms such as, for example, methoxy, ethoxy, propoxy and the like. The term "lower alkylene" as used herein, denotes straight or branched chain aliphatic hydrocarbon groups having 1 to 6 carbon atoms such as methylene, ethylene, butylene, isobutylene and the like. The term "lower acyl" as used herein, denotes acyl groups having from 1 to 6 carbon atoms such as formyl, acetyl, and propionyl. The term "halogen", as used herein, denotes chlorine, bromine, iodine and fluorine. The term "lower alkanol" as used herein, denotes straight or branched chain alkanols having from 1 to 6 carbon atoms such as methanol, ethanol, isopropanol, butanol and the like. The term "aryl" as used herein, denotes unsubstituted mono or polynuclear aryl groups such as phenyl, naphthyl, anthryl, phenanthryl and the like. The term "aryl lower alkyl" as used herein, denotes aryl alkyl groups wherein the aryl and alkyl moieties are as defined above. The term "lower acyloxy" denotes acyloxy groups having 1 to 6 carbon atoms such as formyloxy, acetoxy and propionyloxy. The term "lower alkyl aryl", as used herein denotes alkyl aryl groups wherein the alkyl and aryl moieties are as defined above.

The initial step in the preparation of the compound of formula I involves the preparation of a compound of the following formula:

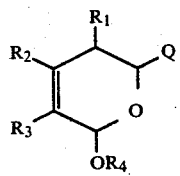

wherein $R_1$, $R_2$, $R_3$ and $R_4$ are as previously defined and Q is formyl,

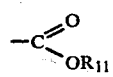

where $R_{11}$ is lower alkyl, and $-CH_2OR_{10}$ where $R_{10}$ is hydrogen or lower acyl; which comprises reacting a compound having the formula:

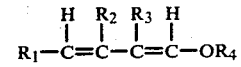

wherein $R_1$, $R_2$, $R_3$ and $R_4$ are as previously defined; with a compound having the formula:

wherein Q is as defined above.

The above reaction may be conducted in the presence or absence of solvent at temperatures varying from about $-15°$ C. to about $+200°$ C. If it is desired to employ a solvent, any inert organic solvent may be used. Typical solvents that may be employed are aliphatic hydrocarbons such as pentane, hexane, heptane, octane and the like; aromatic hydrocarbons such as benzene, xylene, toluene, naphthalene and the like; halogenated hydrocarbons such as methylene chloride, carbon tetrachloride, chlorobenzene and the like; amides such as formamide, dimethylformamide (DMF), tetramethylurea, hexamethylphosphoric acid triamide; ethers such as dioxane, anisole and tetrahydrofuran; nitriles such as acetonitrile, benzonitrile and the like; ketones such as acetone, cyclohexanone and the like. Solvents such as dimethylsulfoxide (DMSO) and N-methylpyrrolidone may also be employed. The above-mentioned solvents may be used singly or in combination.

The Diels-Alder condensation of compounds VI and VII may, optionally be carried out in the presence of a Lewis acid catalyst. The advantages of carrying out the reaction catalytically are an increase in the reaction rate and the capability of carrying out the reaction at lower temperatures. Any conventional Lewis acid may be employed in the condensation.

Preferred embodiments of compound V are compounds having the formula:

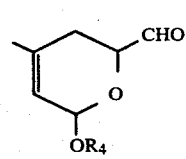 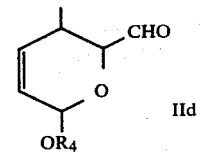

wherein $R_4$ is as previously defined.

Particularly preferred embodiments of compound IIa are when $R_4$ is equal to methyl (IIb) or ethyl (IIc). Preferred embodiments of compound IId are likewise when $R_4$ is equal to methyl (IIe) or ethyl (IIf).

Compound IIa is novel and forms one aspect of the invention. Compound IIa is prepared by reacting 4-methoxyisoprene (1-methoxy-3-methyl-1,3-butadiene) with n-butyl glyoxylate in accordance with the procedures described hereinbefore. The reaction product is a compound having the formula of compound V wherein

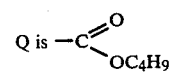

Compound IIa may then be formed by reduction with any chemical reducing agent useful for the conversion of esters to aldehydes such as sodium aluminum hydride or diisobutyl aluminum hydride. Care must be exercised in the choice of reducing agents such that overreduction does not occur. As with the reaction preceding the reduction, compound V may be reduced in the presence or absence of solvent.

Alternatively, compound IIa may be formed by reduction of the compound of formula V wherein

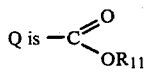 (V)

by reduction with any chemical reducing agent useful for the conversion of esters to alcohols, such as lithium aluminum hydride, sodium aluminum hydride, aluminum hydride, diisobutylaluminum hydride and the like, followed by oxidation of the alcohol produced in the reduction, a compound of the formula V where $Q=-CH_2OH$ (Vc), with any chemical oxidizing agent capable of converting alcohols to aldehydes, such as silver oxide, Jones reagent, etc.

Alternatively, compound IIa may be formed in accordance with the above procedure by reacting 4-methoxyisoprene with glyoxal, thus obviating the need for a subsequent reduction step.

Compound IId is prepared in the same manner as compound IIa with the exception that 1-ethoxypentadiene-1,3 is employed in lieu of 4-methoxyisoprene.

The compound of formula II is subsequently reacted with a compound having the formula:

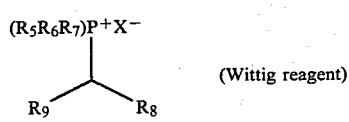

(Wittig reagent)

III wherein $R_5$, $R_6$, $R_7$, $R_8$, $R_9$ and X are as previously defined; to form a compound having the formula:

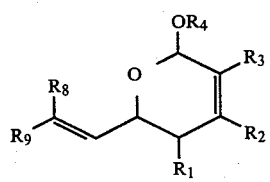

IV wherein $R_1$, $R_2$, $R_3$, $R_4$, $R_8$ and $R_9$ are as previously defined.

Compound IV is then subjected to acid catalysts to yield a compound of formula I.

Compound IV is novel and forms another aspect of this invention. The reaction between compound II and compound III, the well known Wittig reaction, to form compound IV, preferably is carried out in the presence of a solvent, i.e., an organic solvent substantially inert to the reactants, such as a lower alkanol solvent, i.e., methanol, ethanol, etc., dimethylformamide, acetonitrile, tetrahydrofuran, dimethylsulfoxide, hexamethyl phosphoric acid triamide or benzene. The preferred solvents are methanol, isopropanol and dichloromethane, toluene or combinations of the above. The reaction is conducted in the presence of a strong base, such as an alkali metal hydride, e.g., sodium hydride, potassium hydride, an alkali metal amide, e.g., sodium amide, lithium diisopropyl amide, an alkali metal lower alkoxide, preferably sodium methoxide, or solution of an alkali metal hydroxide in a lower alkanol, e.g., KOH in methanol or water. Other strong bases which can be utilized include aryl or alkyl group I-A metallo organic compounds wherein lithium, sodium, and potassium are the preferred metallo moieties and wherein the preferred alkyl moieties are the lower alkyl groups and the preferred aryl moieties are phenyl and lower alkyl substituted phenyl groups. Also included among the bases that may be employed are the hydroxides of alkali and alkaline earth metals such as sodium hydroxide, lithium hydroxide, potassium hydroxide, calcium hydroxide, magnesium and barium hydroxides. The Wittig reagents that may be employed are the well known phosphonium and phosphonate compounds. Typical Wittig reagents used herein are salts of phosphorous compounds such as triphenyl phosphonium chlorides, triphenyl phosphonium bromides, tributylphosphonium chlorides or bromides, tribenylphosphonium chlorides or bromides. Mixed aryl and alkyl phosphonium halides may be employed as well. The Wittig reagent may employ, as well as the halides, other anionic moieties such as $HSO_4^-$ and $NO_3^-$. A particularly preferred Wittig reagent is triphenylphosphonium chloride. Temperatures and pressures are not critical but the reaction is generally carried out at $-30°$ C. to room temperature and atmospheric pressure. Although the Wittig procedure is preferred, the Horner modification of this procedure may also be employed.

A preferred embodiment of compound IV is a compound of the formula:

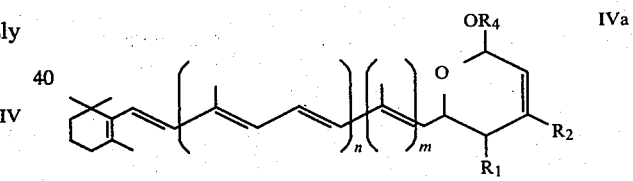

IVa wherein $R_1$, $R_2$, $R_4$, m and n are as previously defined.

Particularly preferred embodiments of compound IVa are compounds having the formulae:

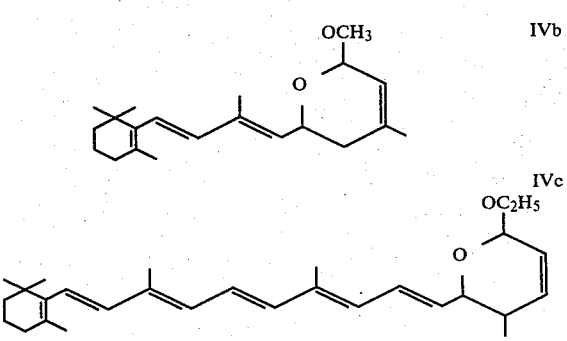

Compounds IVb and IVc are novel thus forming additional aspects of this invention.

Compound IVb is prepared by reacting a compound of the formula:

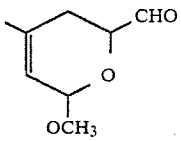

with a compound of the formula:

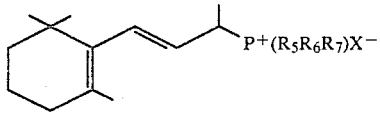

wherein $R_5$, $R_6$, $R_7$ and X are as previously defined; in accordance with the procedure described hereinbefore.

Compound IVc is prepared by reacting a compound of the formula:

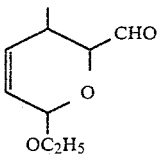

with a compound of the formula:

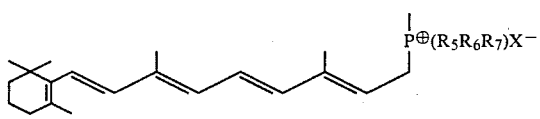

wherein $R_5$, $R_6$, $R_7$ and X are as previously defined; in accordance with the procedure described hereinbefore.

Compounds IVb–IVc are treated with a catalyst to transform them to the corresponding polyene aldehyde. Specifically, compounds IVb and IVc yield retinal and apo-10′-carotenal, respectively, which are well known compounds of the vitamin A and carotenoid series.

Exemplary of the compounds that may be employed as catalysts are lower alkyl and lower alkyl aryl and aryl sulfonic acids such as benzenesulfonic acid, methansulfonic acid and p-toluenesulfonic acid; lower alkyl carboxylic acids such as formic and acetic acids; lower alkyl dicarboxylic acids, such as oxalic acid, may also be employed. Halogenated lower alkyl carboxylic acids such as di- and trihalo acetic acids, e.g., trichloro- and trifluoro-acetic acids, are also usable herein. Acid salts of amine bases, such as hydrohalides of heterocyclic amines particularly pyridine hydrochloride, lower alkyl amine acid salts such as the hydrohalides of triethylamine, aniline, o-toluidine and the like, may also be used. Particularly preferred is pyridine hydrochloride. The reaction is generally carried out in a solvent at temperatures varying from about 75° C. to about 200° C. Typical solvents that may be employed are aliphatic hydrocarbons such as hexane, heptane, octane; aromatic hydrocarbons such as benzene, toluene and xylene. Aprotic solvents such as DMF, DMSO, N-methylpyrrolidone and N,N-dimethylacetamide may also be used. These solvents may be used singly or admixture. A preferred solvent combination is a mixture of DMF with xylene, benzene or toluene.

The procedure disclosed and claimed herein may be carried out continuously or batchwise.

The following nonlimiting examples illustrate the instant invention. All percentages, unless otherwise specified, are by weight. All temperatures are in degrees C.

EXAMPLE 1

Preparation of butyl 4-methyl-6-methoxy-3,6-dihydro-2H-pyran-2-carboxylate

The following example illustrates the preparation of the captioned compound carried out in the absence of solvent.

9.6 g. (0.098 mol) of 4-methoxyisoprene, 11.54 g. (0.089 mol) of butyl glyoxylate, and 0.10 g. of hydroquinone were stirred at 100°–105° for 1.5 hour. Distillation of the crude mixture gave two fractions:

1.04 g, $b_{0.65}=97°$ (90% purity by gc, 4.6% yield) and
15.97 g, $b_{0.5}=97°-100°$ (99+% purity by gc, 78.3% yield).

Anal. calcd. for $C_{12}H_{20}O_4$: C 63.13, H, 8.83; Found: C 63.10, H 8.68.

EXAMPLE 2

This example illustrates the preparation of the compound of Example 1, carried out at room temperature.

A solution of 3.95 g. (0.033 mol) of 4-methoxyisoprene (gc purity 82%), 4.30 g. (0.033 mol) of butyl glyoxylate and a trace of hydroquinone in 20 ml. of methylene chloride was stirred at room temperature for 24 hours to give a solution of the crude 2H-pyran ester. Distillation of the crude ester afforded 5.88 g. (purity 92% by gc) of the 2H-pyran ester (72% yield) as a colorless oil.

EXAMPLE 3

The following example illustrates the obtention of 2-methoxy-4-methyl-5,6-dihydro-2H-pyran-6-carboxaldehyde by reduction of the corresponding esters of Examples 1–2.

To a suspension of sodium aluminum hydride (0.32 g., 6.0 mmol) in 5 ml. of dry THF was added a solution of butyl ester (0.912 g., 4.0 mmol, distilled) in dry THF at 78° under argon and the mixture was stirred at this temperature for 2 hours. One ml. of ethyl acetate was added and followed by 2 ml. of saturated sodium sulfate solution. The mixture was warmed to room temperature and filtered. Evaporation of the solvent afforded 0.61 g. of crude product which was chromatographed on silica gel (35 g.) and eluted with 10–30% of ether in hexane to give 0.33 g. of 2H-pyran aldehyde (53% yield).

Anal. calcd. for $C_8H_{12}O_3$: C 61.52, H 7.75; Found: C 61.66, H 7.77.

EXAMPLE 4

The following example illustrates an alternative procedure for the preparation of the compound of Example 3 by utilizing a Diels-Alder condensation of 4-methoxyisoprene with glyoxal.

Glyoxal hydrate (10.5 g., 0.153 mol glyoxal) in 100 ml. of silicone oil (General Electric SF-96) was added to 800 ml. of silicone oil at 200°–225° with an $N_2$ stream and vigorous stirring ($N_2$ rate 5–8.5 cu. ft./hr.=2.5–3.5 l/hr.). The vapor stream was passed upward through a condenser packed with glass beads onto which 4-methoxylsoprene was being dripped at such rate as to obtain a percolating action in the zone of the condenser. Reaction occurred in the zone of the condenser and glass beads when the 4-methoxyisoprene (15.2 g., 0.155 mol) was added. After the addition (20 minutes) there was 2.34 g. glyoxal untransferred (stopped-up addition funnel). The final product yield of 16.15 grams represents 37% overall yield based on glyoxal.

EXAMPLE 5

Preparation of 2-methoxy-4-methyl-5,6-dihydro-6-[2-methyl-4-(2,6,6-trimethylcyclohexen-1-yl)-buta-1,3-dienyl]-2H-pyran To a solution of the 2H-pyran aldehyde of Example 4, (10.78 g., 5.0 mmol) and β-ionylidene triphenylphonium chloride (3.32 g., 7.0 mmol in 20 ml. of isopropanol at 0° was added a solution of potassium hydroxide (0.39 g., 7.0 mmol) in 2 ml. of water. The mixture was stirred at this temperature for 1½ hour and poured into ice water. The mixture was extracted with two 10 mol-portions of hexane and the combined hexane extract was washed with 5 ml. of 80% aqueous methanol, brine and dried over anhydrous sodium sulfate. Evaporation of the solvent afforded 1.80 g. of crude product which was chromatographed on silica gel (18 g.) and eluted with 1 to 5% of ether in hexane to give 0.76 g. of 2H-pyran (49% yield).

Anal. calcd. for $C_{21}H_{32}O_2$: C 79.70, H 10.19; Found: C 79.78, H 10.41.

EXAMPLE 6

Preparation of retinal from 2-methoxy-4-methyl-5,6-dihydro-6-[2-methyl-4-(2,6,6-trimethylcyclohexen-1-yl)-buta-1,3-dienyl]-2H-pyran All reactions were carried out in a dark room equipped with yellow fluorescent safelamps (Sylvania F-4060) under nitrogen.

The following example illustrates retinal using pyridine hydrochloride as the catalyst.

To a solution of 0.1 g. (0.3 mmol) of the above compound in 1 ml. of a mixture of DMF and aromatic hydrocarbon (1:4 in ratio; xylene, toluene or benzene depending on temperature required) was added at room temperature a measured quantity (0.5-3.0 mole %) of a 1% DMF solution of pyridine hydrochloride (prepared by adding an ether solution of anhydrous hydrogen chloride to a pyridine solution in ether at 0°. The precipitate was collected, washed with ether, and dried under vacuum). The reaction mixture was placed into a preheated oil bath (the temperature was regulated from 80° to 140° as the reaction required) for 5 to 90 minutes, cooled and neutralized with 1 ml. of saturated sodium bicarbonate solution. The organic phase was extracted twice with 2 ml. of ether. The combined organic phase was washed with brine and dried over anhydrous sodium sulfate. Addition of a crystal of BHT followed by evaporation of the solvent afforded 0.09 g. of a brown oily product. The results are given in Table 1.

EXAMPLE 7

The procedure of Example 6 was followed using p-toluenesulfonic acid as catalyst to a solution of 0.1 g. (0.3 mmol) of the compound of Example 6 in 2 ml. of xylene was added a measured quantity (0.0425-0.34 mole%) of a 0.1% solution of p-toluenesulfonic acid in xylene at room temperature. The reaction mixture was placed into a preheated oil bath (140°) for 10 minutes, cooled and neutralized with 2 ml. of saturated sodium bicarbonate solution. The organic layer was separated and the aqueous layer was extracted twice with 2 ml. of ether. The combined organic phase was washed with brine and dried over anhydrous sodium sulfate. Addition of a crystal of BHT followed by evaporation of the solvents afforded 0.08 g. of brown oily product. The results are given in table 1.

TABLE 1

| Pyran | | Catalyst | | | Time | LC Analysis[a] | | | LC[b] | Corrected |
| mmole | purity | (mole %) | Solvent | ml. | Temp. min. | Trans | 13cis | 9cis | Yield % | LC yield % |
| --- | --- | --- | --- | --- | --- | --- | --- | --- | --- | --- |
| 0.3 | chrom. | pyr. HCl (0.5) | Xylene-DMF | 1.0 | 140° 10 | 31 | 49 | 10 | 90 | 83.7 |
| 0.3 | chrom. | pyr. HCl (1.0) | Xylene-DMF | 1.0 | 140° 5 | 36 | 29 | 13.0 | 78 | 72.5 |
| 0.3 | crude | pyr. HCl (1.0) | Xylene-DMF | 1.0 | 140° 10 | 19.4 | 22.2 | 9.0 | 50.6 | 47 |
| 0.3 | chrom. | pyr. HCl (1.0) | Toluene-DMF | 1.0 | 110° 15 | 26 | 56 | 9 | 91 | 84.6 |
| 0.3 | crude | pyr. HCl (1.0) | Toluene-DMF | 1.0 | 110° 10 | 12.9 | 42 | 5.5 | 60.4 | 56.2 |
| 0.3 | chrom. | pyr. HCl (3.0) | Benzene-DMF | 1.0 | 80° 5 | 30 | 31 | 11 | 72 | 67 |
| 0.3 | chrom. | pyr. HCl (1.5) | Benzene-DMF | 1.0 | 80° 20 | 29 | 35 | 10 | 74 | 68.8 |
| 0.3 | chrom. | p-TsOH—$H_2O$ (0.17) | Xylene | 2.0 | 140° 10 | 5 | 38 | 2 | 45 | 41.9 |
| 0.3 | chrom. | p-TsOH—$H_2O$ (0.34) | Xylene | 2.0 | 140° 10 | 16 | 18 | 10 | 44 | 40.9 |
| 0.3 | chrom. | p-TsOH—$H_2O$ (0.085) | Xylene | 2.0 | 140° 10 | 7 | 33 | 4 | 44 | 40.9 |
| 0.3 | chrom. | p-TsoH—$H_2O$ (0.0425) | Xylene | 2.0 | 140° 90 | 9 | 15 | 4 | 28 | 26.0 |
| 0.3 | crude | HOAc/ NaOAc | HOAc | 1.5 | 120° | TLC shows retinal and UV max at 370 mµ | | | | |
| 0.3 | crude | HCOOH (250) | Xylene | 1.5 | 140° | TLC shows retinal and UV max at 370 mµ | | | | |
| 0.3 | crude | $H_2C_2O_4 \cdot 2H_2O$ | Xylene | 1.5 | 140° | TLC shows retinal and UV max at 370 mµ | | | | |

TABLE 1-continued

| Pyran | | Catalyst | | | Time | LC Analysis[a] | | | LC[b] | Corrected |
|---|---|---|---|---|---|---|---|---|---|---|
| mmole | purity | (mole %) | Solvent | ml. | Temp. min. | Trans | 13cis | 9cis | Yield % | LC yield % |
| | (13) | | | | | | | | | |

[a] LC analyses were conducted using an internal standard and crystalline, all trans retinal as a reference standard and ratios for the geometrical isomers.
[b] material balance was virtually quantitative in the reactions using chromatographed pyran and was found to be 90% in the large scale reaction (from crude pyran).

EXAMPLE 8

The procedure of Example 7 was followed by using trichloroacetic acid as catalyst. This example illustrates the preparation of retinal in a continuous mode. A 4"×¼" O.D. column of copper tubing packed with ignited sea sand and solvent (volume approximately 7 ml.) under pressure (500–550 psig) was preheated to 150° in an oven and an 0.4% benzene solution of the compound of Example 6 containing 2–4 mole percent of trichloroacetic acid as catalyst was fed in through a pump at a rate of 200–250 ml/hr under a pressure of 500–550 psig (under such conditions, the maximum contact time was approximately 2 minutes). A total of 150 ml. of a yellow solution was collected, neutralized with sodium bicarbonate solution and dried over anhydrous sodium sulfate. Addition of a crystal BHT followed by evaporation of the solvent afforded a brown oily product. The results are given in Table 1a.

TABLE Ia

The following Table Ia illustrates the preparation of retinal by a continuous mode. The reactions are conducted in columns packed with the materials set forth in the Table.

| Pyran | | Catalyst | | | | Contact | U V | |
|---|---|---|---|---|---|---|---|---|
| mmole | purity | (mole %) | Solvent | Temp. | Column | Time | max. | Est. |
| 0.3 | chrom. | CCl$_3$COOH (4.0) | Benzene | 150° | 4 ft. sea sand | 2.0 min. | 375 (24780) | 56 |
| 0.3 | chrom. | CCl$_3$COOH (2.0) | Benzene | 150° | 4 ft. sea sand | 2.0 min. | 375 (19800) | 46 |
| 0.3 | chrom. | CCl$_3$COOH (2.0) | Benzene | 150° | 4 ft. sea sand | 2.0 min. | 375 (18550) | 40 |
| 0.3 | chrom. | Silica Carrier (Girdler Catalyst) | Hexane | 100° | 2 ft. Silica Carrier | 1.0 min. | 370 | — |

EXAMPLE 9

Preparation of 3,6-dihydro-3-methyl-6-ethoxy-2H-pyran-2-carboxaldehyde

Monomeric glyoxal was generated by heating a mixture of 8.0 g. of glyoxal hydrate (0.117 mol. of monomer) and 48.0 g. of phosphorus pentoxide over a gentle flame over 35 minutes. The liberated monomer was bubbled (argon stream) into 4.8 g. (0.04 mol) of 1-ethoxy-1,3-pentadiene (purity 92.3%) at 120°. After all the monomer had been generated, the solution was heated at 120° for an additional 45 minutes. Distillation afforded 1.32 g. of the pyran (b$_{0.07}$=56°, purity 91%) and 1.86 g. of recovered diene (yield based on diene=32%, based on glyoxal=6.6%).

Anal. calcd for C$_9$H$_{14}$O$_3$: C 63.51, H 8.29, Found: C 63.23, H 8.36.

EXAMPLE 10

Preparation of 2-[4,8-dimethyl-10-(2,6,6-trimethylcyclohexen-1-yl)-1,3,5,7,9-decapentaenyl]-3,6-dihydro-3-methyl-6-ethoxy-2H-pyran To a solution of 1.85 g. (2.82 mmol) of retinyl triphenylphosphonium bisulfate (96%) in 8 ml. of methanol at −15° to −20° was added a sufficient portion of a solution of sodium methoxide (7.18 mmol) in 3 ml. of methanol to produce a deep red color of the ylide. To the solution was added 0.05 g. (2.73 mmol) of the 2H pyran aldehyde of Example 10 in one portion. The remainder of the sodium methoxide solution was added dropwise over 10 minutes keeping the reaction temperature at −15°. The reaction mixture was then stirred at room temperature for 0.5 hour, cooled to −15°, treated with 0.06 ml. of glacial acetic acid and stirred for 15 minutes at −15°−0°. Methanol (7 ml.) and water (23 ml.) were added and the mixture was extracted twice with 25 ml. of petroleum ether. The petroleum ether solution was washed with 70 ml. water and concentrated to give 1.06 g. (92.5%) of oily red-orange crude 2-[4,8-dimethyl-10-(2,6,6-trimethylcyclohexen-1-yl)-1,3,5,7,9-decapentaentyl]-3,6-dihydro-3-methyl-6-ethoxy-2H-pyran as a mixture of isomers u v (hexane): $\lambda_{max}$=347 ($\epsilon$52,900) and 358–9 nm ($\epsilon$52,900) and 358–9 nm ($\epsilon$54,035). Chromatography of a sample of the crude pyran from a different preparation gave analytically pure pyran.

Anal. calcd for C$_{29}$H$_{42}$O$_2$: C 82.41, H 10.02; Found: C 82.62, H 10.19.

EXAMPLE 11

Preparation of apo-10'-carotenal

To a solution of 1.49 g. (3.53 mmol) of the 2H-pyran of Example 11 in 12 ml. of toluene was added a solution of 0.082 g. (0.71 mmol) of pyridine hydrochloride in 3 ml. of anhydrous DMF. The mixture was heated at 90° for 35 minutes, cooled, poured into 30 ml. of ice water and extracted with three portions of petroleum ether (45 ml.). The extracts were washed with 50 ml. of saturated sodium bicarbonate solution, and with two 50-ml. portions of water, dried ($Na_2SO_4$) and concentrated to give 1.31 g. (99%) of crude intensely dark orange solid crude apo-10'-carotenal as a mixture of isomers. Chromatography of 0.789 g. of the crude product on silica gel gave 0.477 g. (60.5%) of pure apo-10'-carotenal as a mixture of isomers.

The following examples illustrate the preparation of 2H-pyran carboxylates within the scope of this invention

EXAMPLE 2

Preparation of butyl-3-methyl-6-alkoxy-3,6-dihydro-2H-pyran-2-carboxylate

A mixture of an alkoxypentadiene, butyl glyoxylate, and hydroquinone or a solution of these compounds in methylene chloride was stirred at the indicated temperature for the time given in Table II. The solvent, where present, was removed by distillation at atmospheric pressure. Further distillation at reduced pressure through a Vigreaux column gave a complete separation of the starting materials and product 2H-pyran butyl ester in the yields indicated in Table II.

TABLE II

| Alkoxy pentadiene (mmole) | n-butyl glyoxylate (mmole) | Temperature | Time | Solvent[a] | Recovered[b] Starting Materials | Yield[c] |
|---|---|---|---|---|---|---|
| 1-methoxy pentadiene 38.5 | 77.0 | 105° | 9 hr | — | — | 55% |
| 1-ethoxy pentadiene 28.0 | 26.4 | 100°–105° | 18.5 hr | — | 1.83 g | 46% |
| 1-ethoxy pentadiene 28.0 | 26.4 | reflux | 47 hr | $CH_2Cl_2$ | 3.81 g | 36% |
| 1-ethoxy pentadiene 29.0 | 32.2 | 120° | 4.5 hr | — | 1.42 g | 40% |
| 1-ethoxy pentadiene 226 | 250 | reflux | 48 hr | $CH_2Cl_2$ | 28.0 g | 34% |

[a] hydroquinone was added to all reaction mixtures
[b] a mixture of diene and butyl glyoxylate
[c] based on limiting reagent.

EXAMPLE 13

Preparation of butyl-3-methyl-6-ethoxy-3,6-dihydro-2H-pyran-2-carboxylate

Following the procedure of Example 12, a solution of 26.7 g. (0.226 mol) of 1-ethoxy-1,3-pentadiene (purity, 95%), 32.5 g. (0.25 mol) of butyl glyoxylate and 0.250 g. of hydroquinone in 250 ml. of methylene chloride was refluxed for 48 hours to give 28.0 g. of a mixture of 1-ethoxy-1,3-pentadiene and butyl glyoxylate and 20.32 g. of distilled 2H-pyran butyl ester ($b_{1.0}$=100°–110°) as an oil. Yield based on 1-ethoxy-1,3-pentadiene, 34%.

EXAMPLE 14

Retinal is prepared according to the procedure of Example 6 with the exception that 0.3 mmole of crude pyran is treated with 0.75 mole% of pyridine hydrochloride in 10 ml. of a xylene/DMF solvent mixture for 20 minutes. The product was obtained in 55.8% yield (corrected to 51.8%) with a distribution of 34.8% trans, 6% 13-cis and 15% 9-cis.

I claim:

1. A process for preparing a compound of the formula:

wherein $R_1$, $R_2$, $R_3$ and $R_8$ each are hydrogen or methyl, $R_9$ is and m and n are 0 or 1; said process comprising treating a compound of the formula:

wherein $R_1$, $R_2$, $R_3$, $R_8$ and $R_9$ are as above and $R_4$ is lower alkyl; with an amine hydrohalide in an aprotic solvent.

2. The process of claim 1 wherein a compound of the formula:

is prepared from a compound of the formula:

3. The process of claim 1 wherein a compound of the formula:
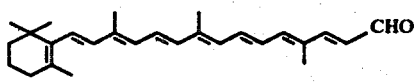
is prepared from a compound of the formula:
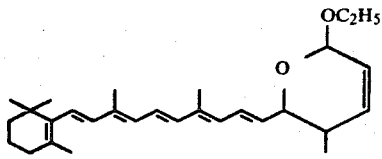
4. The process of claims 1, 2 or 3 wherein the amine hydrohalide is pyridine hydrochloride and said aprotic solvent is benzene, toluene, xylene, dimethylformamide or N-methylpyrrolidinone.
5. The process of claim 4 wherein the process is carried out from about 75° C. to about 200° C.
* * * * *